United States Patent
Biskeborn et al.

(10) Patent No.: US 8,621,910 B2
(45) Date of Patent: Jan. 7, 2014

(54) WEAR GAUGE ARRAY FOR HEAD PROTECTIVE COATING

(75) Inventors: Robert Glenn Biskeborn, Hollister, CA (US); W. Stanley Czarnecki, Palo Alto, CA (US); Jason Liang, Campbell, CA (US); Calvin Shyhjong Lo, Saratoga, CA (US)

(73) Assignee: International Business Machines Corporation, Armonk, NY (US)

( * ) Notice: Subject to any disclaimer, the term of this patent is extended or adjusted under 35 U.S.C. 154(b) by 606 days.

(21) Appl. No.: 12/431,529

(22) Filed: Apr. 28, 2009

(65) Prior Publication Data

US 2010/0269565 A1 Oct. 28, 2010

(51) Int. Cl.
*G01N 3/56* (2006.01)
*G01N 19/02* (2006.01)

(52) U.S. Cl.
USPC .............................. 73/7; 428/810

(58) Field of Classification Search
USPC ............................................................ 73/7
See application file for complete search history.

(56) References Cited

U.S. PATENT DOCUMENTS

| | | | | |
|---|---|---|---|---|
| 3,495,049 | A * | 2/1970 | Humphreys et al. | 360/122 |
| 4,544,960 | A * | 10/1985 | Konishi | 386/120 |
| 4,750,073 | A * | 6/1988 | Saitoh et al. | 360/131 |
| 5,303,574 | A | 4/1994 | Matossian et al. | 73/7 |
| 5,965,896 | A | 10/1999 | Marton | 250/559.4 |
| 6,269,533 | B2 * | 8/2001 | Dugas | 29/603.13 |
| 7,037,607 | B2 | 5/2006 | Ono et al. | 428/848.1 |
| 7,106,544 | B2 * | 9/2006 | Dugas et al. | 360/75 |
| 7,107,694 | B2 | 9/2006 | Yang et al. | 33/18.1 |
| 7,289,202 | B2 | 10/2007 | Groess et al. | 356/239.2 |
| 7,375,327 | B2 | 5/2008 | Yoshiki et al. | 250/310 |
| 2002/0015146 | A1 | 2/2002 | Meeks et al. | 356/73 |
| 2005/0172702 | A1 | 8/2005 | Gitis et al. | 73/81 |

OTHER PUBLICATIONS

Peter L. Blau, "Applications of Microindentation Methods in Tribology Research", 1986, Microindentation Techniques in Materials Science and Engineering, American Society for Testing and Materials, STP 889, pp. 209 and 210.*
D. M. Perry, MSc, PhD; P. J. Moran, BSc; G. M. Robinson, PhD; "Three-dimensional surface metrology of magnetic recording materials through direct-phase-detecting microscope interferometry", 1984, presented at the IERE Conference on Video & Data Recording held at Southhampton.*

(Continued)

*Primary Examiner* — Lisa Caputo
*Assistant Examiner* — Roger Hernandez-Prewitt
(74) *Attorney, Agent, or Firm* — Zilka-Kotab, PC

(57) ABSTRACT

In one embodiment, a system comprises a magnetic head, a protective coating on a media-facing side of the head, and an indentation in the protective coating having a dimension that, when the protective coating wears, is indicative of an amount of wear of the protective coating. A method, in another embodiment, comprises creating an indentation in a protective coating of a magnetic head, the indentation having a dimension that, when the protective coating wears, is indicative of an amount of wear of the protective coating. In another embodiment, a method comprises visually inspecting indentations in a protective coating of a magnetic head, wherein at least two of the indentations have differing dimensions that, when the protective coating wears, are indicative of the amount of wear of the protective coating. The method also includes estimating an amount of wear of the protective coating based on the visual inspection.

19 Claims, 5 Drawing Sheets

(56) References Cited

OTHER PUBLICATIONS

Author: Bharat Bhushan and John A. Lowry, Title: Friction and wear studies of various head materials and magnetic tapes in a linear mode accelereated test using a new nano-scratch wear measurement technique, Date: Nov. 1995, Publisher: Elsevier Science B.V., Volume: 190, Issue 1, pp. 1-6 of 15.*

Peter L. Blau, "Applications of Microindentation Methods in Tribology Research", 1986, Microindentation Techniques in Materials Science and Engineering, American Society for Testing and Materials, STP 889, pp. 209-211.*

Author: Bharat Bhushan and John A. Lowry, Title: Friction and wear studies of various head materials and magnetic tapes in a linear mode accelereated test using a new nano-scratch wear measurement technique, Date: Nov. 1995, Publisher: Elsevier Science B.V., Volume: 190, Issue 1, pp. 1-15 of 15.*

Author: Bharat Bhushan and B. K. Gupta, Title: "Developement of Hard Carbon Coatings for Thin-Film Tape Heads", Date: Nov. 1995, Vol: 31, No. 6, pp. 2976-2978.*

Authors: Bharat Bhushan, Steven T. Patton, Ramesh Sundaram and Subrata Dey, Title: "Pole tip recession studies of hard carbon-coated thin-film tape heads", Date: Apr. 15, 1996, Publisher: American Institute of Physics, Publication: Journal of Applied Physics, 79 , pp. i and 5916-5918.*

Authors: J. A. L. Potgiesser and J. Koorneef, Title: "Mechanical wear and degeneration of the magnetic properties of magnetic heads caused by the tape", Date: Jun. 1974, Publication: The Radio and Electronic Engineer. vol. 44, No. 6, pp. 313-318.*

Authors: Bharat Bhushan, B.K. Gupta, Ramesh Sundaram, Subrata Dey et al., Title: "Developement of Hard Carbon Coatings for Thin-Film Tape Heads", Date: Nov. 1995, Publisher and Publication: IEEE Transactions on Magnetics, Vol. 31, No. 6, pp. 2976-2978.*

Sivertsen, J.M. et al., "Evaluation of amorphous diamond-like carbon-nitrogen films as wearprotective coatings on thin film media and thin film head sliders" IEEE Transactions on Magnetics, vol. 33, No. 1, Jan. 1997; abstract only.

"A new method for evaluating the scratch resistance of diamond-like carbon films by the nano-scratch technique" 08357203; INSPEC Abstract No. : A2002-19/8170-009; abstract only.

* cited by examiner

400

402 Create an indentation in a protective coating of a magnetic head, the protective coating covering at least one of a reader and a writer of the magnetic head, the indentation having a dimension that, when the protective coating wears, is indicative of an amount of wear of the protective coating

502 Visually inspect indentations in a protective coating of a magnetic head, the protective coating covering a media-facing side of at least one of a reader and a writer, wherein one of the indentations has different dimensions than a second of the indentations spaced therefrom, wherein the dimensions of the indentations are indicative of the amount of wear of the protective coating

504 Estimate an amount of wear of the protective coating based on the visual inspection

WEAR GAUGE ARRAY FOR HEAD PROTECTIVE COATING

BACKGROUND

The present invention relates to data storage systems, and more particularly, this invention relates to protective coating systems for magnetic head components.

In magnetic storage systems, data is read from and written onto magnetic recording media utilizing magnetic transducers commonly. Data is written on the magnetic recording media by moving a magnetic recording transducer to a position over the media where the data is to be stored. The magnetic recording transducer then generates a magnetic field, which encodes the data into the magnetic media. Data is read from the media by similarly positioning the magnetic read transducer and then sensing the magnetic field of the magnetic media. Read and write operations may be independently synchronized with the movement of the media to ensure that the data can be read from and written to the desired location on the media.

An important and continuing goal in the data storage industry is that of increasing the density of data stored on a medium. For tape storage systems, that goal has led to increasing the track density on recording tape, and decreasing the thickness of the magnetic tape medium. However, the development of small footprint, higher performance tape drive systems has created various problems in the design of a tape head assembly for use in such systems.

In a tape drive system, magnetic tape is moved over the surface of the tape head at high speed. This movement generally entrains a film of air between the head and tape. Usually the tape head is designed to minimize the spacing between the head and the tape. The spacing between the magnetic head and the magnetic tape is crucial so that the recording gaps of the transducers, which are the source of the magnetic recording flux, are in near contact with the tape to effect efficient signal transfer, and so that the read element is in near contact with the tape to provide effective coupling of the magnetic field from the tape to the read element.

In hard disk and tape magnetic heads, a protective coating is often employed to protect the read and/or write sensors from corrosion, shorting, and excessive wear. The coating may be composed of any hard substance, but generally diamond-like carbon (DLC), silicon nitride, alumina, and other hard materials are used. The thickness of the coating is usually on the order of a few nanometers to tens of nanometers. Currently, there is no quick and easy method of determining the actual thickness of the coating. During the fabrication of the head, the thickness of the coating on the air bearing surface (ABS) is one factor to be considered in the placement of other components of the hard disk or tape system. Also, during drive or tape operation, it would be beneficial to known the thickness of the coating remaining on the head and therefore, evaluate the life of the coating.

Current methods such as Focused Ion Beam/Transmission Electron Microscopy (FIB/TEM) analysis suffer significant drawbacks of being tedious, time consuming, and destructive. Elipsometry is another method to determine thickness of head coatings, but it requires modeling and can sometimes be inaccurate. Accordingly, a better thickness determination method and wear gauge is desirable that overcomes the drawbacks of current methods of determining coating thicknesses on magnetic heads.

SUMMARY

In one embodiment, a system comprises a magnetic head, a protective coating on a media-facing side of the head, and an indentation in the protective coating having a dimension that, when the protective coating wears, is indicative of an amount of wear of the protective coating.

A method, in another embodiment, comprises creating an indentation in a protective coating of a magnetic head, the indentation having a dimension that, when the protective coating wears, is indicative of an amount of wear of the protective coating.

In another embodiment, a method comprises visually inspecting indentations in a protective coating of a magnetic head, wherein at least two of the indentations have differing dimensions that, when the protective coating wears, are indicative of the amount of wear of the protective coating. The method also includes estimating an amount of wear of the protective coating based on the visual inspection.

Any of these embodiments may be implemented in a magnetic data storage system (e.g., tape drive system, hard disk drive system, etc.) which may include a magnetic head, a drive mechanism for passing a magnetic medium (e.g., recording tape, hard disk, etc) over the magnetic head, and a controller electrically coupled to the magnetic head.

Other aspects and embodiments of the present invention will become apparent from the following detailed description, which, when taken in conjunction with the drawings, illustrate by way of example the principles of the invention.

BRIEF DESCRIPTION OF THE SEVERAL VIEWS OF THE DRAWINGS

FIG. 4 is a flow diagram of a method according to one embodiment.

FIG. 5 is a flow diagram of a method according to one embodiment.

DETAILED DESCRIPTION

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

The following description discloses several preferred embodiments of tape-based storage systems, as well as operation and/or component parts thereof.

In one general embodiment, a system comprises a magnetic head; a protective coating on a media-facing side of the head; an indentation in the protective coating having a dimension that, when the protective coating wears, is indicative of an amount of wear of the protective coating.

In another general embodiment, a method comprises creating an indentation in a protective coating of a magnetic head, the indentation having a dimension that, when the protective coating wears, is indicative of an amount of wear of the protective coating.

In another general embodiment, a method comprises visually inspecting indentations in a protective coating of a magnetic head, wherein at least two of the indentations have differing dimensions that, when the protective coating wears, are indicative of the amount of wear of the protective coating; and estimating an amount of wear of the protective coating based on the visual inspection.

Figure 1:
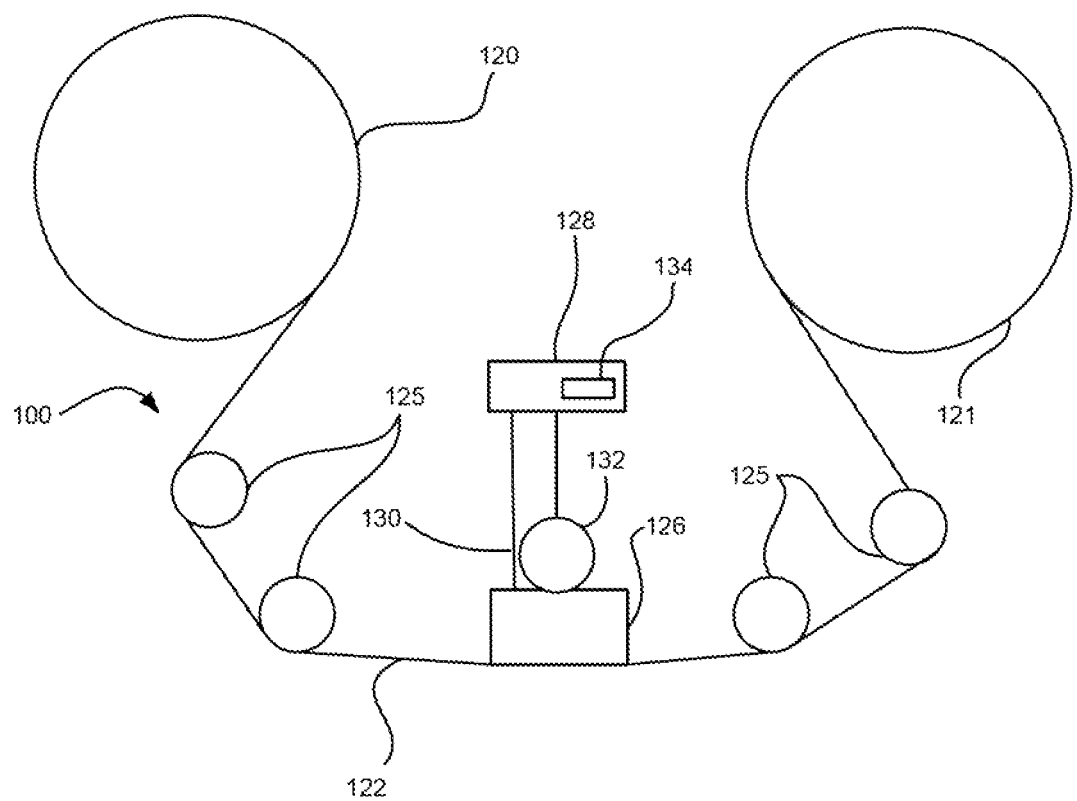
FIG. 1 is a schematic diagram of a simplified tape drive system according to one embodiment.

FIG. 1 illustrates a simplified tape drive 100 of a tape-based data storage system, which may be employed in the context of the present invention. While one specific implementation of a tape drive is shown in FIG. 1, it should be noted that the embodiments described herein may be implemented in the context of any type of tape drive system.

As shown, a tape supply cartridge 120 and a take-up reel 121 are provided to support a tape 122. One or more of the reels may form part of a removable cassette and are not necessarily part of the system 100. The tape drive, such as that illustrated in FIG. 1, may further include drive motor(s) to drive the tape supply cartridge 120 and the take-up reel 121 to move the tape 122 over a tape head 126 of any type.

Guides 125 guide the tape 122 across the tape head 126. Such tape head 126 is in turn coupled to a controller assembly 128 via a cable 130. The controller 128 typically controls head functions such as servo following, writing, reading, etc. The cable 130 may include read/write circuits to transmit data to the head 126 to be recorded on the tape 122 and to receive data read by the head 126 from the tape 122. An actuator 132 controls position of the head 126 relative to the tape 122.

An interface 134 may also be provided for communication between the tape drive and a host (integral or external) to send and receive the data and for controlling the operation of the tape drive and communicating the status of the tape drive to the host, all as will be understood by those of skill in the art.

Figure 2:
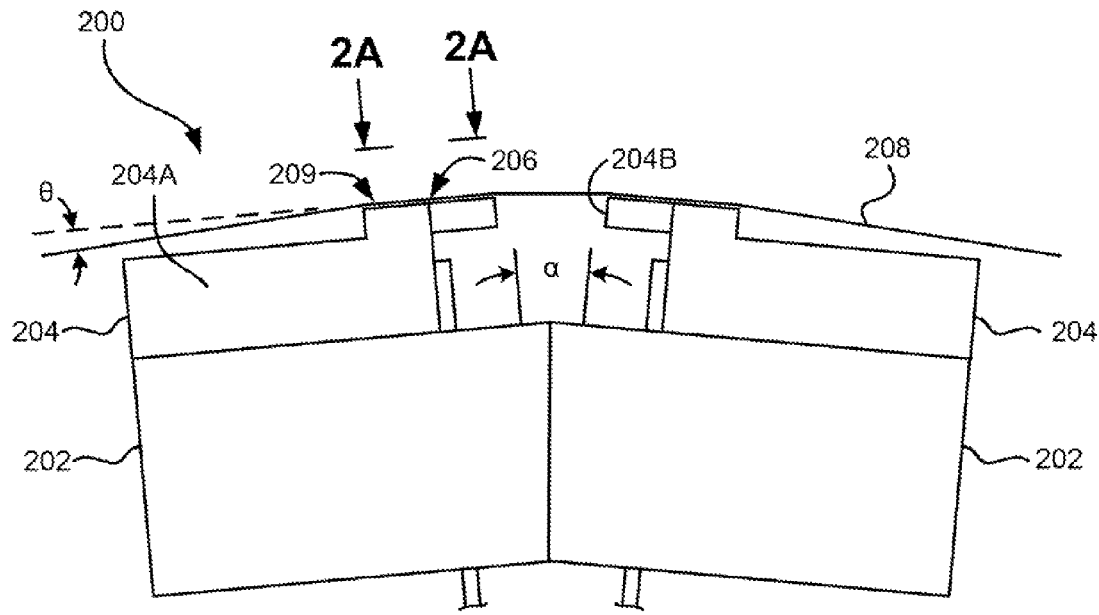
FIG. 2 illustrates a side view of a flat-lapped, bi-directional, two-module magnetic tape head according to one embodiment.

By way of example, FIG. 2 illustrates a side view of a flat-lapped, bi-directional, two-module magnetic tape head 200 which may be implemented in the context of the present invention. As shown, the head includes a pair of bases 202, each equipped with a module 204, and fixed at a small angle α with respect to each other. The bases are typically "U-beams" that are adhesively coupled together. Each module 204 includes a substrate 204A and a closure 204B with a gap comprising elements 206 such as readers and/or writers situated therebetween. In use, a tape 208 is moved over the modules 204 along a media (tape) bearing surface 209 in the manner shown for reading and writing data on the tape 208 using the readers and writers. The wrap angle θ of the tape 208 at edges going onto and exiting the flat media support surfaces 209 are usually between ⅛ degree and 4½ degrees.

The substrates 204A are typically constructed of a wear resistant material, such as a ceramic. The closures 204B made of the same or similar ceramic as the substrates 204A.

The readers and writers may be arranged in a piggyback configuration. The readers and writers may also be arranged in an interleaved configuration. Alternatively, each array of channels may be readers or writers only. Any of these arrays may contain one or more servo readers.

Figure 2A:
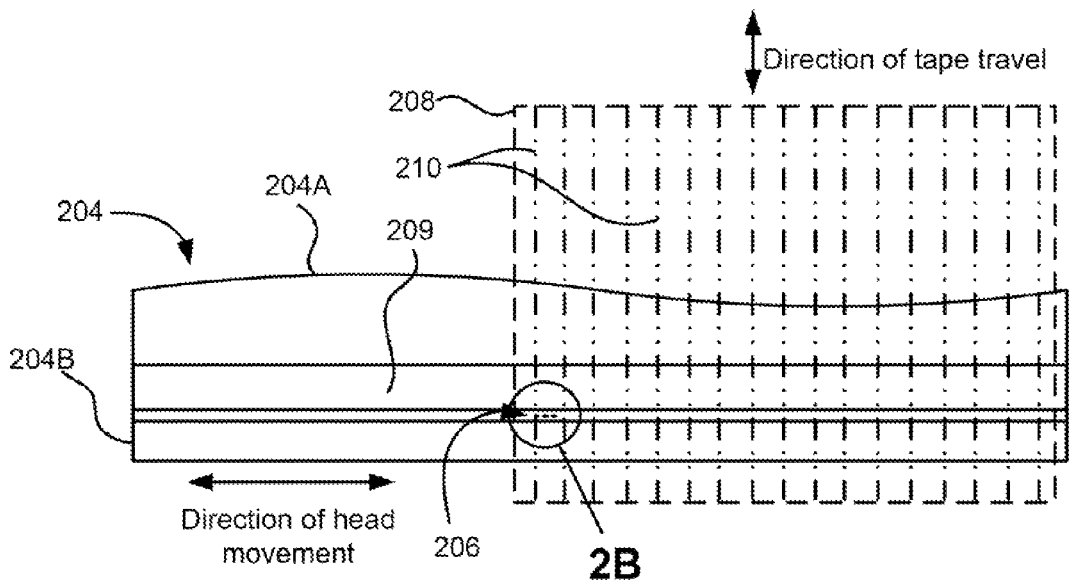
FIG. 2A is a tape bearing surface view taken from Line 2A of FIG. 2.

FIG. 2A illustrates the tape bearing surface 209 of one of the modules 204 taken from Line 2A of FIG. 2. A representative tape 208 is shown in dashed lines. The module 204 is preferably long enough to be able to support the tape as the head steps between data bands.

In this example, the tape 208 includes 4-22 data bands, e.g., with 16 data bands and 17 servo tracks 210, as shown in FIG. 2A on a one-half inch wide tape 208. The data bands are defined between servo tracks 210. Each data band may include a number of data tracks, for example 96 data tracks (not shown). During read/write operations, the elements 206 are positioned within one of the data bands. Outer readers, sometimes called servo readers, read the servo tracks 210. The servo signals are in turn used to keep the elements 206 aligned with a particular track during the read/write operations.

Figure 2B:
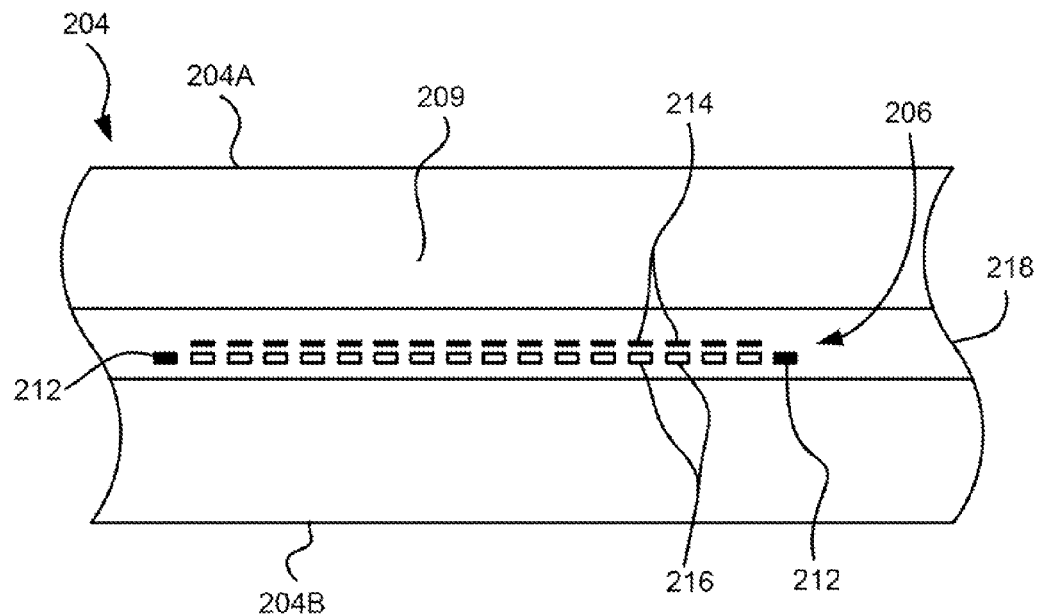
FIG. 2B is a detailed view taken from Circle 2B of FIG. 2A.

FIG. 2B depicts a plurality of read and/or write elements 206 formed in a gap 218 on the module 204 in Circle 2B of FIG. 2A. As shown, the array of elements 206 includes, for example, 16 writers 214, 16 readers 216 and two servo readers 212, though the number of elements may vary. Illustrative embodiments include 8, 16, 32, and 64 elements 206 per array. A preferred embodiment includes 32 readers per array and/or 32 writers per array. This allows the tape to travel more slowly, thereby reducing speed-induced tracking and mechanical difficulties. While the readers and writers may be arranged in a piggyback configuration as shown in FIG. 2B, the readers 216 and writers 214 may also be arranged in an interleaved configuration. Alternatively, each array of elements 266 may be readers or writers only, and the arrays may contain one or more servo readers 212. As noted by considering FIGS. 2 and 2A-B together, each module 204 may include a complementary set of elements 206 for such things as bi-directional reading and writing, read-while-write capability, backward compatibility, etc.

Figure 2C:
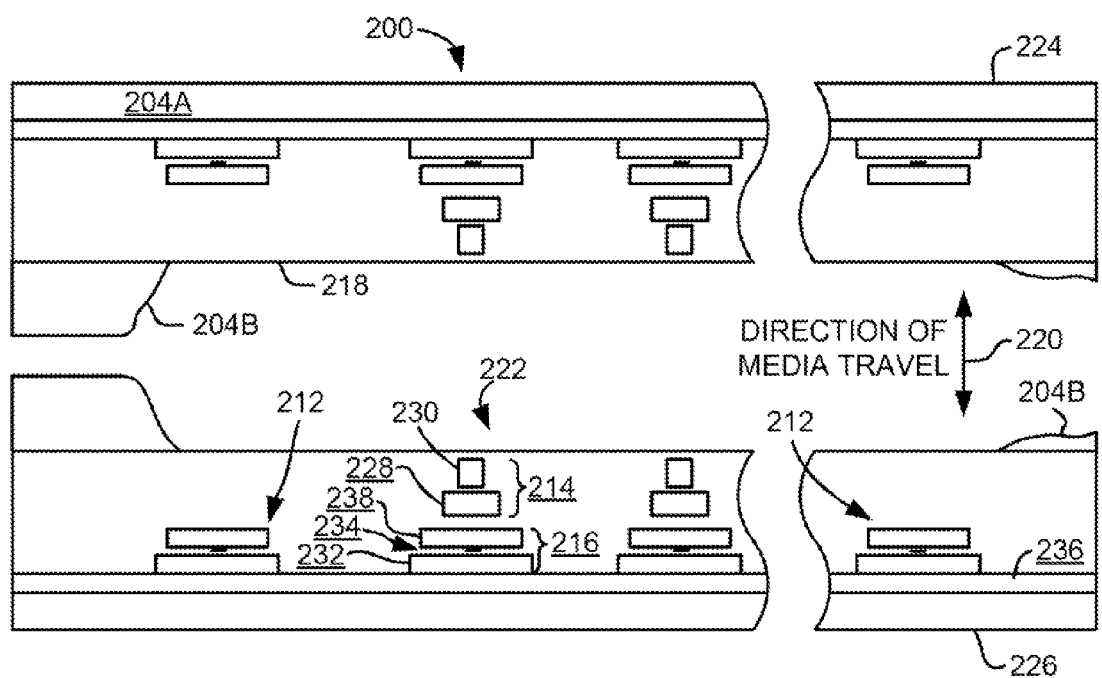
FIG. 2C is a detailed view of a partial tape bearing surface of a pair of modules.

FIG. 2C shows a partial tape bearing surface view of complimentary modules of a magnetic tape head 200 according to one embodiment. In this embodiment, each module has a plurality of read/write (R/W) pairs in a piggyback configuration formed on a common substrate 204A and an optional electrically insulative layer 236. The writers, exemplified by the write head 214 and the readers, exemplified by the read head 216, are aligned parallel to a direction of travel of a tape medium thereacross to form an R/W pair, exemplified by the R/W pair 222.

Several R/W pairs 222 may be present, such as 8, 16, 32 pairs, etc. The R/W pairs 222 as shown are linearly aligned in a direction generally perpendicular to a direction of tape travel thereacross. However, the pairs may also be aligned diagonally, etc. Servo readers 212 are positioned on the outside of the array of R/W pairs, the function of which is well known.

Generally, the magnetic tape medium moves in either a forward or reverse direction as indicated by arrow 220. The magnetic tape medium and head assembly 200 operate in a transducing relationship in the manner well-known in the art. The piggybacked MR head assembly 200 includes two thin-film modules 224 and 226 of generally identical construction.

Modules 224 and 226 are joined together with a space present between closures 204B thereof (partially shown) to form a single physical unit to provide read-while-write capability by activating the writer of the leading module and reader of the trailing module aligned with the writer of the leading module parallel to the direction of tape travel relative thereto. When a module 224, 226 of a piggyback head 200 is constructed, layers are formed in the gap 218 created above an electrically conductive substrate 204A (partially shown), e.g., of AlTiC, in generally the following order for the R/W pairs 222: an insulating layer 236, a first shield 232 typically of an iron alloy such as NiFe (permalloy), CZT or Al—Fe—Si (Sendust), a sensor 234 for sensing a data track on a magnetic medium, a second shield 238 typically of a nickel-iron alloy (e.g., 80/20 Permalloy), first and second writer pole tips 228, 230, and a coil (not shown).

The first and second writer poles 228, 230 may be fabricated from high magnetic moment materials such as 45/55 NiFe. Note that these materials are provided by way of example only, and other materials may be used. Additional layers such as insulation between the shields and/or pole tips and an insulation layer surrounding the sensor may be present. Illustrative materials for the insulation include alumina and other oxides, insulative polymers, etc.

In some embodiments, the invention provides a fast, easy, and accurate method and/or system of determining the thickness and wear rate of a coating material. An array of indentations may be created on the surface of the coating. These indentations may be of increasing depth and/or size created by a very fine instrument point, such as a diamond tip, which may be pushed into the coating with increasing force to form the indentations. The indentations may be equally spaced apart and easily identifiable by interferometry and/or profiling. Multiple rows of indentations can be created either of varying size indentations or duplicates of previous rows so that there is less chance of the measurement being affected by an indentation getting filled in with debris.

Indentations can also be made across multiple shields, poles, and other layers to evaluate whether the coating is depleted more quickly on one layer than another. Additionally, the indentations across multiple layers may give an indication of the material properties of that layer. As a wear gauge, the method may be used to evaluate the coating after a certain amount of runtime of the drive. Wear rates can be estimated based on the physical size of the indentations, remaining depth of the grooves, and even the number of indentations left.

For example, if an array of 5 indentations of increasing depth from 10 nm to 50 nm was created on a coating of 50 nm thickness, it is possible to tell the approximate remaining thickness of the coating just by counting the number of indentations left. After a certain amount of time, if 20 nm of the coating has been worn away, the indentations made at 10 and 20 nm depth will have been worn away also. At a later point in time, if no indentations are left, one can conclude that all the coating in that area has been removed.

Figure 3A:
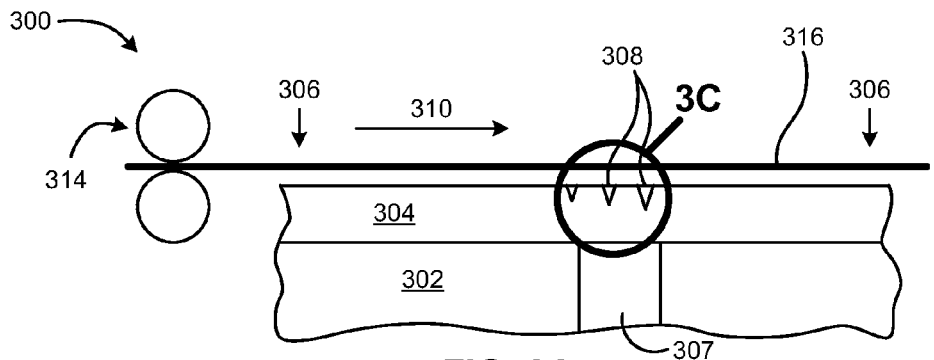
FIG. 3A shows a side view of a system for determining the wear of a protective coating on a magnetic head according to one embodiment.
Figure 3B:
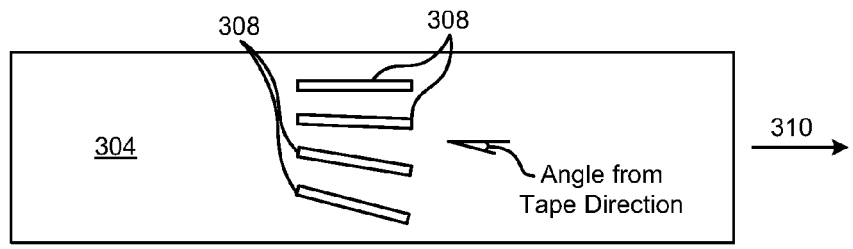
FIG. 3B is a top view of a system for determining the wear of a protective coating on a magnetic head according to one embodiment.
Figure 3C:
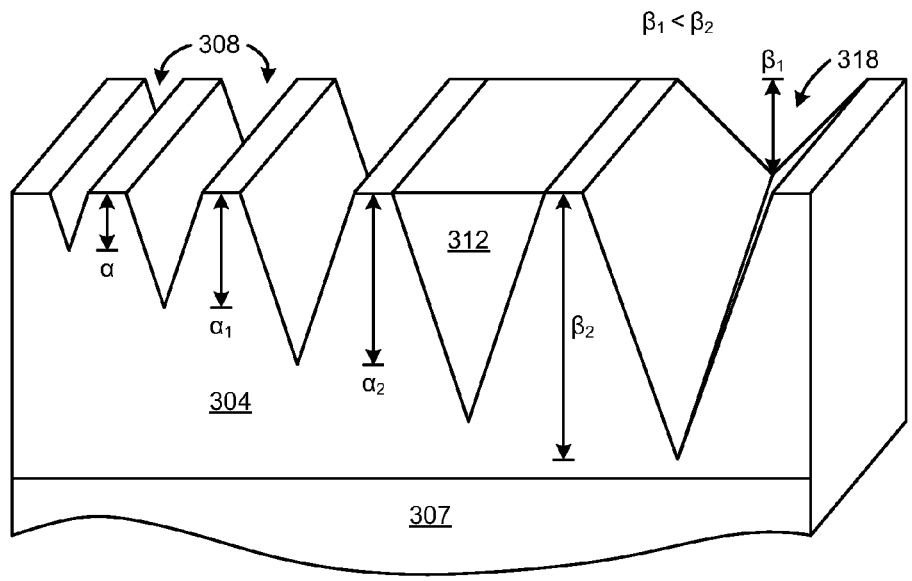
FIG. 3C is a detailed perspective view taken from Circle 3C in FIG. 3A.

With reference to FIGS. 3A-3C, in one embodiment, a system 300 for determining the thickness of coatings on a magnetic head includes a magnetic head 302 which may have a protective coating 304 on a media-facing side of the head 302, such as the ABS side of the head (the ABS side is designated by arrows 306) above a media-facing side of the at least one of a reader 307 and a writer of the magnetic head 302. Also, the system 300 may include an indentation 308 of any shape in the protective coating 304 having a dimension a that, when the protective coating 304 wears, is indicative of an amount of wear of the protective coating 304.

In some embodiments, the system 300 may include several indentations 308 of any shape (e.g., triangular, square, rectangular, elliptical, etc.) that may be present in the protective coating 304, wherein at least two of the indentations 308 have differing dimensions $a_1$, $a_2$ that, when the protective coating 304 wears, are indicative of the amount of wear of the protective coating 304. For example, shallower indentations will disappear faster than deeper indentations.

In some approaches, the indentations may include channels or depressions having different depths or channels which start out at one depth on one end and increase in depth towards the other end. Also, as shown in FIG. 3B, the indentations may include channels running in a direction greater than 0°, preferably greater than about 2°, more preferably greater than about 5° from a direction of media travel thereover. The direction of media travel is indicated by arrow 310. In some further approaches, the channels may run in a direction less than about 90° from the direction of media travel thereover, as indicated by arrow 310.

In some embodiments, system 300 may further comprise an indentation 308 on a second portion of the head 302 having a different composition than the protective coating 304, such as a substrate, a closure, a second area of protective coating, etc.

In some more embodiments, as shown in FIG. 3C, a fill material 312 may be present in one or more indentations 308. This fill material 312 may have special characteristics or properties, such that it may be detected with a sensing device, visually different from the protective coating 304, able to reflect certain wavelengths of light differently from the protective coating 304, etc. For example, a fill material may be of a type that can emit small amounts of detectable radioactive energy, such as cesium, uranium, etc., such that as the fill material is worn away, less and less detectable radioactive energy is emitted from the fill material left in the indentation. In this manner, the height of the remaining indentation can be determined without examining the indentation itself. Any other type of fill material may also be used, and this example is not limiting in any manner.

With continued reference to FIG. 3C, in some approaches, one or more of the indentations 308 may include a channel 318 having a varying depth along a length thereof. For example, the indentation 308 may be V-shaped in profile, and the lower point of the V may descend deeper into the protective coating 304 as the profile is examined along the length of the channel 318. In some of these approaches, the channel 318 may rise to the surface of the protective coating 304 and descend to the surface of the magnetic head 302, but any depth including and between these values is possible.

System 300, according to some embodiments, may further comprise a drive mechanism 314 for passing a magnetic recording tape 316 over the head 302. In addition, the system 300 may include a controller in communication with the head 302.

With reference to FIG. 4, a method 400 according to one embodiment may be described. Of course, the method may be used in any desired environment, and is not limited in any way by being described in accordance with FIGS. 3A-3C. The method 400 comprises creating an indentation of any shape in a protective coating of a magnetic head, such as those shown in FIG. 3, e.g., covering at least one of a reader and a writer of the magnetic head, the indentation having a dimension that, when the protective coating wears, is indicative of an amount of wear of the protective coating. Note operation 402.

In some embodiments, the method may further comprise filling the indentation with a fill material. The fill material may have properties and/or characteristics which make it more easily detectable against the background of the protective coating.

In some approaches, several indentations of any shape may be created in the protective coating, wherein at least two of the indentations may have differing dimensions that, when the protective coating wears, are indicative of the amount of wear of the protective coating. In further approaches, the indentations may include channels or depressions having different depths. In addition, as shown in FIG. 3B, the indentations may include channels running in a direction greater than 0°, preferably greater than about 2°, more preferably greater than about 5° from a direction of media travel thereover, as indicated by arrow 310.

In some more embodiments, the method may further comprise creating an indentation on a second portion of the head having a different composition than the protective coating. In this manner, the thickness and wear rate of two different materials or compositions may be detected, so that comparisons may be made between the two materials, wear rates may be detected across different surfaces of the magnetic head, etc.

In some more embodiments, one or more of the indentations may include a channel having a varying depth along a length thereof, such that the level of wear may be detected from a single indentation.

In even more embodiments, referring to FIG. 5, a method 500 for determining wear on a magnetic head may comprise, in operation 502, visually inspecting indentations in a protective coating of a magnetic head, e.g., covering at least one of a reader and a writer of the magnetic head, wherein at least two of the indentations have differing dimensions that, when the protective coating wears, are indicative of the amount of wear of the protective coating. Also, the method may include, in operation 504, estimating an amount of wear of the protective coating based on the visual inspection. In addition, in some embodiments, the method may further comprise generating an electronic report indicative of the estimated amount of wear of the protective coating. For example, after the indentations have been visually inspected, possibly by an optical device coupled with a computing device, a graph, plot, spreadsheet, etc., may be produced which includes depths, times, dates, materials, different head designations, etc., so that wear rates and material wear resistance may be determined and/or compared.

It will be clear that the various features of the foregoing methodologies may be combined in any way, creating a plurality of combinations from the descriptions presented above.

While various embodiments have been described above, it should be understood that they have been presented by way of example only, and not limitation. Thus, the breadth and scope of an embodiment of the present invention should not be limited by any of the above-described exemplary embodiments, but should be defined only in accordance with the following claims and their equivalents.

What is claimed is:

1. A system, comprising:
a magnetic head having a planar media-facing side;
a protective coating on a media-facing side of the head above a media-facing side of the at least one of a reader and a writer of the magnetic head;
an indentation in the protective coating having a dimension that, when the protective coating wears, is indicative of an amount of wear of the protective coating, wherein the indentation includes a channel having a progressively increasing depth along a length thereof.

2. The system of claim 1, wherein several indentations are present in the protective coating, the indentations being spatially separated from each other on the media-facing side of the protective coating, wherein at least two of the indentations have differing dimensions that, when the protective coating wears, are indicative of the amount of wear of the protective coating.

3. The system of claim 2, wherein the indentations include channels or depressions, a first of the indentations having a depth at least 10 nm greater than a second of the indentations.

4. The system of claim 1, wherein at least one of the indentations includes a channel running in a direction greater than 5 degrees and less than 85 degrees from a direction of media travel thereover.

5. The system of claim 1, wherein the at least one of the reader and the writer are positioned in a gap sandwiched between a substrate and a closure of the magnetic head.

6. The system of claim 1, further comprising an indentation on a second portion of the head, the second portion of the head having a different material composition than the protective coating, the indentation on the second portion of the head having a dimension that, when the second portion of head wears, is indicative of an amount of wear of the second portion of the head.

7. The system of claim 1, further comprising a fill material in the indentation, wherein the fill material is visibly different than the protective coating.

8. The system of claim 1, wherein the indentation extends from an opening at a media-facing side of the protective coating into the protective coating toward the head, wherein the indentation does not extend completely through the protective coating.

9. The system as recited in claim 1, further comprising:
a drive mechanism for passing a magnetic recording tape over the head; and
a controller in communication with the head.

10. A method, comprising:
creating several indentations in a protective coating of a magnetic head, the protective coating covering at least one of a reader and a writer of the magnetic head, at least two of the indentations having predefined differing dimensions that, when the protective coating wears, are indicative of an amount of wear of the protective coating, at least one of the indentations including a channel having a progressively increasing depth along a length thereof; and
selecting the differing dimensions prior to the creating, thereby predefining the differing dimensions.

11. The method of claim 10, wherein the indentations include channels running in a direction greater than 0 degrees from an intended direction of media travel thereover, the indentations being spatially separated from each other on the media-facing side of the protective coating.

12. The method of claim 10, further comprising filling the indentation.

13. The method of claim 10, wherein the indentations include channels or depressions having different predefined depths.

14. The method of claim 10, further comprising creating an indentation on a second portion of the head, the second portion of the head having a different material composition than the protective coating, the indentation on the second portion of the head having a dimension that, when the second portion of head wears, is indicative of an amount of wear of the second portion of the head.

15. The method of claim 10, wherein the indentation includes a channel having a progressively increasing depth along a length thereof.

16. A method, comprising:
visually inspecting indentations in a protective coating of a magnetic head, the protective coating covering a media-facing side of at least one of a reader and a writer, wherein one of the indentations has different dimensions than a second of the indentations spaced therefrom, wherein the one of the indentations includes a channel having a progressively increasing depth along a length thereof, wherein the dimensions of the indentations are indicative of the amount of wear of the protective coating; and estimating an amount of wear of the protective coating based on the visual inspection.

17. The method of claim 16, further comprising generating an electronic report indicative of the estimated amount of wear of the protective coating, wherein the protective coating covers at least one of a reader and a writer of the magnetic head.

18. A system, comprising:
a magnetic head;
a drive mechanism for passing a magnetic recording tape over the head;
a controller in communication with the head;
a protective coating on a media-facing side of the head;
several indentations in a media-facing side of the protective coating, each of the indentations having a dimension that, when the protective coating wears, is indicative of an amount of wear of the protective coating, the indentations being spatially separated on the media-facing side of the protective coating,
wherein the indentations include channels or depressions, a first of the indentations having a different predefined depth than a second of the indentations, at least one of the indentations including a channel having a progressively increasing depth along a length thereof.

19. The system of claim 18, wherein at least one of the indentations includes a channel running in a direction greater than 5 degrees and less than 85 degrees from a direction of media travel thereover.

\* \* \* \* \*